(12) United States Patent
Imperiale

(10) Patent No.: US 6,867,022 B1
(45) Date of Patent: Mar. 15, 2005

(54) REPLICATION DEFICIENT ADENOVIRUS VECTORS AND METHODS OF MAKING AND USING THEM

(75) Inventor: Michael J. Imperiale, Ann Arbor, MI (US)

(73) Assignee: Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 09/488,867

(22) Filed: Jan. 21, 2000

(51) Int. Cl.$^7$ .............................................. C12N 15/64
(52) U.S. Cl. .................... 435/91.4; 435/455; 435/456; 435/325; 435/457; 435/471; 435/475; 435/369; 435/320.1; 424/93.2
(58) Field of Search ........................... 435/320.1, 455, 435/325, 456, 457, 471, 475, 369, 91.4, 367, 368, 370, 91.41, 91.42, 69.1; 424/93.2, 193.21; 514/44

(56) References Cited

U.S. PATENT DOCUMENTS

| | | | |
|---|---|---|---|
| 5,851,806 A | 12/1998 | Kovesdi et al. | 435/91.41 |
| 5,880,102 A | 3/1999 | George et al. | 514/44 |
| 5,882,877 A | 3/1999 | Gregory et al. | 435/320.1 |
| 5,891,690 A | 4/1999 | Massie | 435/172.3 |
| 5,919,676 A | 7/1999 | Graham et al. | 435/172.3 |
| 5,922,576 A | 7/1999 | He et al. | 435/91.41 |
| 5,981,225 A | 11/1999 | Kochanek et al. | 435/69.1 |
| 5,985,846 A | 11/1999 | Kochanek et al. | 514/44 |
| 5,994,132 A | 11/1999 | Chamberlain et al. | 435/369 |
| 5,994,134 A | 11/1999 | Giroux et al. | 435/403 |
| 6,001,557 A | 12/1999 | Wilson et al. | 435/5 |

FOREIGN PATENT DOCUMENTS

| | | | |
|---|---|---|---|
| EP | 0 955 373 | 11/1999 | C12N/15/86 |
| EP | 0 978 566 | 2/2000 | C12N/15/86 |
| WO | WO 96/33280 | 10/1996 | C12N/15/86 |
| WO | WO 97/32481 | 9/1997 | A01N/63/00 |
| WO | WO 98/13510 | 4/1998 | C12N/15/86 |
| WO | WO 99/32647 | 7/1999 | C12N/15/86 |
| WO | WO99/41400 | 8/1999 | C12N/15/86 |
| WO | WO 99/53085 | 10/1999 | C12N/15/86 |

OTHER PUBLICATIONS

T–L Chiu et al.,Folding & Design, "Optimizing energy potentials for success in protein tertiary structure prediction," May 1998, 3:223–228.*
Rubanyi, The future of human gene therapy, 2001, Molecular Aspects of Medicine, vol. 22, pp. 113–142.*
Imperiale, Molecular biology of adenovirus gene therapy vectors, 2000, Basic Science and Gene Therapy, pp. 119–128.*
Danthinne et al., Production of first generation adenovirus vectors: a review, 2000, Gene Therapy, vol. 7, pp. 1707–1714.*
Hasson et al., Adenovirus L1 52– and 55–kilodalton proteins are required for assembly of virions, 1989, Journal of Virology, pp. 3612–3621.*
Gustin et al., Encapsidation of viral DNA requires the adenovirus L1 52/55–kilodalton protein, 1998, Journal of Virology, pp. 7860–7870.*
Zhang et al., Interaction of the adenovirus IVa2 protein with viral packaging sequences, 2000, Journal of Virology, pp. 2687–2693.*
Schmid et al., Bipartite structure and functional independence of adenovirus type 5 packaging elements, 1997, Journal of Virology, pp. 3375–3384.*
Gustin et al., Interaction of the adenovirus L1 52/55–kilodation protein with the IVa2 gene product during infection, 1996, Journal of Virology, vol. 70, pp. 6463–6467.*
Verma et al., Gene therapy–promises, problems and prospects, 1997, NATURE, vol. 389, pp. 239–242.*
Anderson, Human gene therapy, 1998, NATURE, vol. 392, pp. 25–30.*
Parks et al., "Use of helper–dependent adenoviral vectors of alternative serotypes permits repeat vector administration," *Gene Therapy*, (1999) 6, 1565–1573.
Mayr et al., "Development of Replication–Defective Adenovirus Serotype 5 Containing the Capsid and 3C Protease Coding Regions of Foot–and–Mouth Disease Virus as a Vaccine Candidate," *Virology* 263 (1999) 496–506.
Nabel, "Development of optimized vectors for gene therapy," *Proc. Natl. Acad. Sci. USA*, vol. 96, (Jan. 1999), pp. 324–326.
Schmid et al., "Cellular components Interact with Adenovirus Type 5 Minimal DNA Packaging Domains," *Journal of Virology* (Aug. 1998) p. 6339–6347.
Alemany et al., "Complementation of helper–dependent adenoviral vectors: size effects and titer fluctuations," *Journal of Virological Methods* 68, (1997) p. 147–159.
Schmid et al., "Bipartite Structure and Functional Independence of Adenovirus Type 5 Packaging Elements," *Journal of Virology* (May 1997) p. 3375–3384.
Fechteler et al., "The Mechanism of Adenovirus DNA Integration: Studies in a Cell–Free System," *Curr. Top. Microbial. Immunol.* (1995) 199 (Pt. 2): 109–137.
Schmid et al., "Selective Encapsidation of Adenovirus DNA," *Curr. Top. Microbial. Immunol.* (1995) 199 (Pt. 1): 67–80.
Grable et al., "cis and trans Requirements for the Selective Packaging of Adenovirus Type 5 DNA," *Journal of Virology* (Feb. 1992) p. 723–731.

* cited by examiner

Primary Examiner—Scott D. Priebe
Assistant Examiner—Brian Whiteman
(74) Attorney, Agent, or Firm—Medlen & Carroll, LLP

(57) ABSTRACT

The invention provides novel replication deficient adenovirus vectors and methods for making and using these viruses. The invention also provides vector systems and kits using a serotype specific strategy for making adenoviral vector preparations substantially free of replication competent "helper" virus. The helper virus-free preparations provide novel pharmaceutical compositions substantially free of helper virus for use in gene transfer and gene therapy.

25 Claims, 1 Drawing Sheet wt: ATG CAT CCG GTG CTG CGG CAG ATG CGC CCC CCT CCT CAG CAG
wt: M   H   P   V   L   R   Q   M   R   P   P   P   Q   Q wt: CGG CAA GAG CAA GAG CAG CGG CAG ACA TGC AGG GCA
wt: R   Q   E   Q   E   Q   R   Q   T   C   R   A
mt:         t       ct      ta
mt:         *       *       *

*FIG. 1*

SEQUENCE LISTING

```
<160> NUMBER OF SEQ ID NOS: 2

<210> SEQ ID NO 1
<211> LENGTH: 78
<212> TYPE: DNA
<213> ORGANISM: Homo sapiens
<220> FEATURE:
<221> NAME/KEY: CDS
<222> LOCATION: (1)...(78)

<400> SEQUENCE: 1 atg cat ccg gtg ctg cgg cag atg cgc ccc cct cct cag cag cgg caa      48
Met His Pro Val Leu Arg Gln Met Arg Pro Pro Pro Gln Gln Arg Gln
 1               5                  10                  15 gag caa gag cag cgg cag aca tgc agg gca                              78
Glu Gln Glu Gln Arg Gln Thr Cys Arg Ala
             20                  25

<210> SEQ ID NO 2
<211> LENGTH: 26
<212> TYPE: PRT
<213> ORGANISM: Homo sapiens

<400> SEQUENCE: 2

Met His Pro Val Leu Arg Gln Met Arg Pro Pro Pro Gln Gln Arg Gln
 1               5                  10                  15

Glu Gln Glu Gln Arg Gln Thr Cys Arg Ala
             20                  25
```

REPLICATION DEFICIENT ADENOVIRUS VECTORS AND METHODS OF MAKING AND USING THEM

STATEMENT AS TO FEDERALLY-SPONSORED RESEARCH

The United States Government has certain rights in this invention pursuant to grant no. GM34902 awarded by National Institutes of Health, DHHS.

FIELD OF THE INVENTION

This invention generally pertains to the fields of virology, medicine and gene therapy. In particular, this invention provides novel replication deficient adenovirus vectors and vector systems and methods for making and using these viruses. The compositions and methods of the invention are used to make replication defective adenoviral gene therapy vector preparations that are substantially free of replication competent helper viruses.

BACKGROUND OF THE INVENTION

Adenovirus vectors have become important tools in gene therapy and for the in vivo and ex vivo cell-targeted transfer of heterologous, therapeutic genes to diseased cells or tissues, including the treatment of genetic diseases and cancer. Several properties make adenovirus advantageous gene therapy vectors. They can be produced in high titer stocks. Adenovirus can infect resting and nondividing cells, such as dendritic cells and neurons. The adenoviral genome, which is a linear, double-stranded DNA, can be manipulated to accommodate foreign genes that range in size, including reasonably large DNA inserts. They can be re-targeted to a variety of cells. They do not require host cell proliferation to express adenoviral or transgene-encoded proteins. There are no known associations of human malignancies with adenoviral infections despite common human infection with adenoviruses. As adenoviral vectors do not insert into the chromosome of a cell the effect is impermanent and less likely to interfere with the cell's normal function. Live adenovirus has been safely used for many years for human vaccines. Human adenoviruses have been used in humans as in vivo gene delivery vehicles.

However, available adenoviruses can also present serious problems when used in vivo. One drawback to adenovirus-mediated gene therapy is that decreases in gene expression are typically observed after about two weeks following administration of the vector. This loss of expression may require re-administration of the viral vector. If the same adenovirus serotype is re-administered, the host may generate neutralizing antibodies against the fiber or hexon proteins of the viral vector. Such a serotype specific anti-adenovirus response may prevent effective re-administration of the viral vector.

If viral replication is not desired, as with most gene therapy treatments, use of replication competent human adenoviruses is also problematic. For example, infection both in vivo and in vitro with the adenoviral vector can result in cytotoxicity to target cells due to the accumulation of penton protein, which is toxic to mammalian cells. Thus, in gene therapy, replication incompetent or replication defective (transgene-containing) adenovirus genomes are preferred over replication competent forms.

One approach to make a replication defective adenovirus is to inhibit viral DNA replication by disabling at least one necessary viral gene. Many currently available gene therapy adenovirus vectors are inactivated by deletion of the viral early gene region 1, (or "E1 gene"), E2A gene, E2B gene, or E4 gene. Complementation of the disabled gene by a second source will allow replication of the disabled virus. A commonly used method of complementation involves introducing the disabled (transgene-containing) adenoviral genomes into an adenoviral replication competent host cell that stably expresses the missing or mutated viral gene (e.g., the E1 gene). However, this approach has a significant risk in that the defect in the disabled genome can be replaced by homologous recombination with a wild type sequence to produce a replication competent variant.

To address problems created by homologous recombination with wild type sequences adenoviruses have been disabled by deleting most, if not virtually all, viral genes. Adenoviral vectors with only inverted terminal repeats flanking the genome (for DNA replication), an adenoviral packaging signal (to effect insertion of the completed viral genome into a completed viral capsid) and a heterologous transgene have been constructed. In this scheme, to replace the deleted viral genomic sequences a "helper" virus with the necessary complementary genes is expressed (co-transfected or co-infected) with the disabled virus in a host cell. However, this model of adenovirus disabling and complementation is inherently flawed because significant amounts of the "helper" (replication competent) adenovirus can be inadvertently encapsidated. Attempts to decrease the amount of helper partial deletion of the packaging signal in the helper virus. However, helper virus outgrowth still is a problem with these schemes.

Rapid advances in gene therapy have created a great demand for safe and effective adenoviral gene transfer vectors, particularly replication defective constructs. However, current methods for making replication defective adenoviral gene therapy vectors do not adequately address the problem of "helper outgrowth" contamination by replication competent virions. The present invention addresses these and other needs.

SUMMARY OF THE INVENTION

The present invention provides novel vectors and vector systems and methods for selectively packaging adenovirus nucleic acid sequences as replication defective virions based on adenovirus serotype. The serotype specific strategy prevents or actively blocks contamination of adenovirus replication defective vector preparations by replication competent helper viruses.

The invention provides a vector system for selectively packaging a replication defective adenovirus nucleic acid sequence in an adenovirus capsid based on adenovirus serotype, comprising: a first replication defective adenovirus sequence comprising a first adenovirus serotype cis-acting packaging sequence and a heterologous nucleic acid; a second replication defective adenovirus sequence comprising a second adenovirus serotype cis-acting packaging sequence, lacking the ability to produce a polypeptide having the activity of a second adenovirus serotype 52/55 kDa trans-acting protein; and a nucleic acid sequence encoding a polypeptide having the activity of a first adenovirus serotype 52/55 kDa trans-acting protein and lacking the activity of a second adenovirus serotype 52/55 kDa trans-acting protein. In this vector system, the adenovirus capsid, packaging and/or 52/55 kDa trans-acting protein encoding sequences can be human adenovirus sequences. In this system, the first and second adenovirus serotypes can be adenovirus type 2 (Ad2), adenovirus type 5 (Ad5), adenovirus type 7 (Ad7), adenovirus type 12 (Ad12), adenovirus type 17 (Ad17), or adenovirus type 40 (Ad40), and the first serotype differs from the second serotype. In alternative embodiments, the first adenovirus serotype is adenovirus type 5 and the second adenovirus serotype is adenovirus type 7, or, the first adenovirus serotype is adenovirus type 7 and the second adenovirus serotype is adenovirus type 5.

In one embodiment, the first replication defective adenovirus sequence cannot produce a complete adenovirus capsid, e.g., because the defective adenovirus sequence lacks a nucleic acid needed to produce a complete adenovirus capsid. In alternative embodiments, the first replication defective adenovirus sequence is encapsidated in a capsid comprising at least one polypeptide encoded by the second replication defective adenovirus sequence, or, the first replication defective adenovirus sequence is encapsidated in a capsid encoded by the second replication defective adenovirus sequence. The replication defective adenovirus can comprise a defective or modified adenovirus E1 gene, E2A gene, E2B gene, E3 gene, E4 gene, E4 promoter, a penton gene, a fiber gene or a hexon polypeptide gene or a combination thereof.

In one embodiment of the vector system of the invention, the inability to produce a functional 52/55 kDa trans-acting protein is due to a mutation in the sequence encoding the protein. The mutation can be a missense mutation, a point mutation, a frameshift mutation or a deletion mutation.

In another embodiment, the second replication defective adenovirus sequence can further comprise a nucleic acid sequence encoding a polypeptide having the activity of the first serotype 52/55 kDa trans-acting protein.

The nucleic acid sequence encoding the polypeptide having the activity of the first serotype 52/55 kDa trans-acting protein can further comprise an adenovirus replication competent host cell. The adenovirus replication competent host cell can be, e.g. a 293 cell line.

In the vector system of the invention, the polypeptide having the activity of a first serotype 52/55 kDa trans-acting protein can be a first serotype 52/55 kDa trans-acting protein.

In one embodiment, the first replication defective adenovirus sequence can lack at least one nucleic acid sequence needed to produce a capsid and can further comprise a nucleic acid sequence encoding a polypeptide having the activity of a first adenovirus serotype 52/55 kDa trans-acting protein.

The invention also provides a vector system for selectively packaging a replication defective adenovirus nucleic acid sequence in an adenovirus capsid based on adenovirus serotype, comprising: a first replication defective adenovirus sequence comprising a first adenovirus serotype cis-acting packaging sequence and a heterologous nucleic acid; and, a second replication defective adenovirus sequence comprising a second adenovirus serotype cis-acting packaging sequence, a nucleic acid sequence encoding a polypeptide having the activity of a first adenovirus serotype 52/55 kDa trans-acting protein, lacking the ability to produce a polypeptide having the activity of a second adenovirus serotype 52/55 kDa trans-acting protein.

The invention also provides a vector system for selectively packaging a replication defective adenovirus nucleic acid sequence in an adenovirus capsid based on adenovirus serotype, comprising: a first replication defective adenovirus sequence comprising a first adenovirus serotype cis-acting packaging sequence and a heterologous nucleic acid; a second replication defective adenovirus sequence comprising a second adenovirus serotype cis-acting packaging sequence, lacking the ability to produce a polypeptide having the activity of a second adenovirus serotype 52/55 kDa trans-acting protein; and, a cell comprising a nucleic acid sequence encoding a polypeptide having the activity of a first adenovirus serotype 52/55 kDa trans-acting protein.

The invention also provides a vector system for selectively packaging a replication defective adenovirus nucleic acid sequence in an adenovirus capsid based on adenovirus serotype, comprising: a first replication defective adenovirus sequence comprising a first adenovirus serotype cis-acting packaging sequence and a heterologous nucleic acid; a second replication defective adenovirus sequence comprising a second adenovirus serotype cis-acting packaging sequence, lacking the ability to produce a polypeptide having the activity of a second adenovirus serotype 52/55 kDa trans-acting protein; and, an expression cassette comprising a nucleic acid sequence encoding a polypeptide having the activity of a first adenovirus serotype 52/55 kDa trans-acting protein.

The invention also provides a vector comprising a replication defective adenovirus sequence comprising a first adenovirus serotype cis-acting packaging sequence, a nucleic acid sequence encoding a functional second adenovirus serotype 52/55 kDa trans-acting protein, wherein the second adenovirus serotype 52/55 kDa trans-acting protein does not have the activity of a first adenovirus serotype 52/55 kDa trans-acting protein; lacking the ability to produce a polypeptide having the activity of a first adenovirus serotype 52/55 kDa trans-acting protein. In alternative embodiments, the vector can further comprise at least one adenoviral nucleic acid sequence needed to produce an adenoviral capsid, or, it can comprise sufficient adenoviral nucleic acid sequence to produce a complete adenoviral capsid when the vector is expressed in an adenovirus replication-competent host cell. The first and second adenovirus serotypes can be adenovirus type 2 (Ad2), adenovirus type 5 (Ad5), adenovirus type 7 (Ad7), adenovirus type 12 (Ad12), adenovirus type 17 (Ad17), or adenovirus type 40 (Ad40), and the first serotype differs from the second serotype. In alternative embodiments, the first adenovirus serotype is adenovirus type 5 and the second adenovirus serotype is adenovirus type 7, or, the first adenovirus serotype is adenovirus type 7 and the second adenovirus serotype is adenovirus type 5.

The invention also provides a transformed or isolated infected cell comprising the vector system or vector of the invention.

The invention also provides a kit for making adenovirus encapsidated replication defective sequences comprising: a first adenovirus serotype cis-acting packaging sequence and a heterologous nucleic acid, a second replication defective adenovirus sequence comprising a second adenovirus serotype cis-acting packaging sequence, lacking the ability to produce a polypeptide having the activity of a second adenovirus serotype 52/55 kDa trans-acting protein, and, a nucleic acid sequence encoding a polypeptide having the activity of a first adenovirus serotype 52/55 kDa trans-acting protein.

In the kit, the nucleic acid sequence encoding a polypeptide having the activity of a first adenovirus serotype 52/55 kDa trans-acting protein can further comprise an adenovirus replication competent cell. The nucleic acid sequence encoding a polypeptide having the activity of a first adenovirus serotype 52/55 kDa trans-acting protein can further comprise an expression cassette. The second replication defective adenovirus sequence can further comprise the nucleic acid sequence encoding a polypeptide having the activity of a first adenovirus serotype 52/55 kDa trans-acting protein.

The invention also provides a method of producing a replication defective encapsidated adenovirus gene transfer vector, comprising the following steps: (a) transforming or infecting into adenovirus replication competent host cells (i) a first replication defective adenovirus sequence comprising a first adenovirus serotype cis-acting packaging sequence and a heterologous gene, (ii) a second replication defective adenovirus sequence comprising a second adenovirus serotype cis-acting packaging sequence, lacking the ability to produce a polypeptide having the activity of a second adenovirus serotype 52/55 kDa trans-acting protein, and, (iii) a nucleic acid sequence encoding a polypeptide having the activity of a first adenovirus serotype 52/55 kDa trans-acting protein; and, (b) culturing the cells under conditions where the first replication defective adenovirus sequence is encapsidated to produce a replication defective adenovirus gene transfer vector.

The invention also provides a method of producing a replication defective encapsidated adenovirus gene transfer vector, comprising the following steps: (a) transforming or infecting into an adenovirus replication competent host cell two adenovirus replication defective sequences, wherein the cell comprises a nucleic acid sequence encoding a polypeptide having the activity of a first adenovirus serotype 52/55 kDa trans-acting protein, (i) a first replication defective adenovirus sequence comprising a first adenovirus serotype cis-acting packaging sequence and a heterologous gene, and, (ii) a second replication defective adenovirus sequence comprising a second adenovirus serotype cis-acting packaging sequence, lacking the ability to produce a polypeptide having the activity of a second adenovirus serotype 52/55 kDa trans-acting protein; and, (b) culturing the cells under conditions where the first replication defective adenovirus sequence is encapsidated to produce a replication defective adenovirus gene transfer vector.

The invention also provides a method of producing a replication defective encapsidated adenovirus gene transfer vector, comprising the following steps: (a) transforming or infecting into an adenovirus replication competent host cell two adenovirus replication defective sequences (i) a first replication defective adenovirus sequence comprising a first adenovirus serotype cis-acting packaging sequence, a heterologous gene and a nucleic acid sequence encoding a polypeptide having the activity of a first adenovirus serotype 52/55 kDa trans-acting protein, and, (ii) a second replication defective adenovirus sequence comprising a second adenovirus serotype cis-acting packaging sequence, lacking the ability to produce a polypeptide having the activity of a second adenovirus serotype 52/55 kDa trans-acting protein; and, (b) culturing the cells under conditions where the first replication defective adenovirus sequence is encapsidated to produce a replication defective adenovirus gene transfer vector.

In these methods of the invention, the second replication defective adenovirus sequence can further comprise sufficient adenoviral nucleic acid sequence to encode a complete adenoviral viral capsid.

The invention also provides a vector for selectively packaging replication defective nucleic acid sequences in adenovirus capsids based on adenovirus serotype, comprising a replication defective adenovirus sequence comprising an adenovirus serotype 7 (Ad7) cis-acting packaging sequence, a nucleic acid sequence encoding a polypeptide having the activity of an adenovirus serotype 5 (Ad5) 52/55 kDa trans-acting protein, and sufficient adenoviral nucleic acid sequence to encode a viral capsid, lacking the ability to produce a polypeptide having the activity of an adenovirus 7 serotype 52/55 kDa trans-acting protein.

The invention also provides a pharmaceutical composition comprising an encapsidated replication defective adenovirus, made using the vector system of claim 1, substantially free of helper virus, and a pharmaceutically acceptable excipient. In alternative embodiments, the pharmaceutical composition is 100%, 99.99%, 99.98%, 99.97%, 99.95%, 99.93%, 99.9%, 99.5%, 99%, 98%, 97%, 95%, and 90% pure of helper virus.

The invention also provides a method of delivering a heterologous nucleic acid to a cell comprising transforming or infecting a cell with the pharmaceutical composition of the invention. The pharmaceutical composition can be administered to a patient systemically, regionally or locally.

A further understanding of the nature and advantages of the present invention is realized by reference to the remaining portions of the specification, the figures and claims.

All publications, patents and patent applications cited herein are hereby expressly incorporated by reference for all purposes.

BRIEF DESCRIPTION OF THE DRAWINGS

FIG. 1 shows the sequence of the N-terminus of the Ad5 52/55 kilodalton protein open reading frame (ORF) in upper case letters (SEQ ID NO:1); directly below is the corresponding amino acid sequence (SEQ ID NO:2). Below that in lower case are the point mutations that introduce a series of stop codons, indicated by asterisks.

DETAILED DESCRIPTION

The present invention provides a novel strategy to produce preparations of safe and effective replication defective adenovirus (Ad) that are substantially free of replication competent forms. Such "helper virus"-free preparations are particularly useful as gene transfer vectors and gene therapy vectors for administration as pharmaceuticals. The invention is based on the discovery that the mechanism by which the adenovirus packages its newly replicated genome into a newly formed capsid is dependent on serotype specific cis- and trans-acting packaging factors.

A first step in adenovirus replication is the separate synthesis of a complete viral genome and a complete viral capsid: The completed genome is then inserted, or "packaged," into the finished capsid. The exact mechanism used by the virus to package a completed genome into a completed capsid to make a mature virion is not known. However, it is known that packaging of the adenovirus genome requires at least two elements.

First, there is a specific set of sequences, or motifs, mapping at the left end of the genome, which serve as the viral packaging signal. Adenoviral genomes without a packaging signal will not be inserted into a capsid structure. This packaging signal region can contain at least five functionally redundant domains, called "A repeats" (see, e.g., Grable (1990) J. Virol. 64:2047–2056; Grable (1992) J. Virol. 66:723–731). "A repeats" contain consensus motifs that may be able to function independently (Schmid (1997) J. of Virol. 71:3375–3384; Schmid (1998) J. Virol. 71:3375–3384). These motifs appear to be conserved among different adenovirus serotypes.

Second, a soluble trans-acting protein factor of about 52 to 55 kilodaltons (kDa), called the "52/55 kDa protein," must be present during the replication process to form mature virions, i.e., capsids containing complete adenoviral genomes. Exactly how the 52/55 kDa protein is involved in the genome encapsulation process is not known. A trans-acting protein may bind directly, alone or with another protein, to the packaging signal. However, if a functional 52/55 kDa protein is not present, the completed adenoviral genome will not be inserted into a finished capsid structure (see, e.g., Gustin (1998) J. Virol. 72:7860–7870). The 52/55 kDa proteins show significant homology from serotype to serotype over most of the molecule; however, there are less well-conserved sequences at the amino and carboxyl termini (K. Gustin, Ph.D. Thesis, University of Michigan, 1998). These non-conserved amino and carboxyl termini may be involved in the serotype-specific binding of 52/55 kDa protein to cis-acting sequences or other trans-acting factors.

As published findings have reported that "A repeat" motifs appear conserved among different adenovirus serotypes and that the 52/55 kDa protein shows fairly limited homology from serotype to serotype, it was a surprising discovery that the adenoviral packaging cis- and trans-elements act in a serotype specific manner. For example, adenoviral type 7 (Ad7) serotype 52/55 kDa protein will not support genome encapsidation in combination with an adenoviral type 5 (Ad5) serotype packaging signal. The invention for the first time combines a replication defective gene therapy vector having a first cis-acting packaging signal with a helper virus having a second cis-acting packaging signal, wherein the gene therapy vector encodes a 52/55 kDa trans-acting protein only able to support the packaging activity of a first cis-acting packaging signal (leaving the helper virus without a functional encapsidation apparatus).

Typically, the 52/55 kDa trans-acting protein only able to support the packaging activity of the second cis-acting packaging signal is a 52/55 kDa polypeptide derived from the same serotype as that of the second cis-acting signal. This novel strategy provides a means of making replication defective virion preparations substantially free of replication competent "helper" virus (i.e., little to no "helper outgrowth" contamination). Thus, the invention provides novel adenoviral vectors and vectors systems for producing replication deficient vectors. It also provides novel means of making and using these vectors.

Definitions

Unless defined otherwise, all technical and scientific terms used herein have the meaning commonly understood by a person skilled in the art to which this invention belongs. As used herein, the following terms have the meanings ascribed to them unless specified otherwise.

The term "adenovirus" or "Ad" includes all adenoviruses, including all members of the known six subgenera, classified as A to F, and the 47 known distinct human serotypes, as described in detail below. The term "adenovirus serotype" means the individual members of this viral genus that are defined and identified by their expression of at least one serotype-specific epitope. The invention incorporates the different cis- and trans-acting Ad genome packaging factors from all Ad serotypes, including all human and non-human strains.

The term "adenovirus serotype cis-acting packaging sequence" means the set of sequences mapping at the left end of the Ad genome which serve as cis-acting, serotype-specific packaging signals for inserting the Ad genome (or any nucleic acid comprising the packaging signal) into a complete Ad viral capsid, as described in detail below. The term includes the cis-acting packaging signal sequences of any size or variation that retain their packaging and serotype specific characteristics. The term includes the cis-acting packaging signal sequences from any serotype, including those from strains whose packaging factors have not been characterized in detail; these cis- (and trans-) acting packing factors can be identified either by sequence identity (homology) to known cis-acting packaging signal nucleic acid from other serotypes and/or by functional assays, as described in detail below.

The term "adenovirus serotype 52/55 kDa trans-acting protein" or "52/55 kDa protein" means a soluble trans-acting protein factor that must be present during the Ad replication process to complement the above-described cis-acting packaging signal to encapsidate the Ad genome in a serotype specific manner. The term includes polypeptides that are actually 52 to 55 kDa in size and functional (serotype specificity and packaging) equivalents, which can include smaller fragments of the wild type polypeptide. The term includes 52/55 kDa protein-encoding sequences from any serotype, including those from strains whose packaging factors have not been characterized in detail; these can be identified either by sequence identity (homology) to previously characterized 52/55 proteins from other to serotypes and/or by functional assays, as described in detail below.

The phrase "polypeptide having the activity of a second adenovirus serotype 52/55 kDa trans-acting protein" includes any polypeptide that has the trans-acting packaging activity (i.e., ability to support encapsidation with the cis-acting sequence) of a second adenovirus serotype 52/55 kDa trans-acting protein but not (to a significant degree) the packaging activity of a first adenovirus serotype 52/55 kDa trans-acting protein. The invention is based on the surprising finding that a cis-acting packaging signal does not act in conjunction with a trans-acting 52/55 kDa polypeptide from any serotype; it will only package Ad genomes when matched with a 52/55 kDa polypeptide from the same (or a limited set of) serotypes. For example, an Ad5 cis-acting packaging sequence will be complemented by an Ad5 a trans-acting 52/55 kDa polypeptide but not (to a significant degree) by an Ad7 a trans-acting 52/55 kDa polypeptide. Thus, one exemplary vector system of the invention includes a gene therapy vector with an Ad5 cis-acting packaging signal and a helper virus with an Ad7 cis-acting packaging signal, with the system complemented by only an Ad5 a trans-acting 52/55 kDa polypeptide. However, a trans-acting 52/55 kDa polypeptide from another serotype may also be able to significantly complement the Ad5 cis-acting sequence. It can be used in that capacity in the compositions and methods of the invention as long as it cannot also complement (to a significant degree) the cis-acting sequence in the helper virus (the Ad7 cis-acting sequence in this example). Determining if a cis-acting sequence from one serotype can or cannot be functionally complemented by a trans-acting factor from another serotype can be determined by routine screening of cis- and trans-acting packaging factors (and variations thereof) derived from different serotypes using methods described herein.

The term "heterologous" when used with reference to a nucleic acid, indicates that the nucleic acid is in a cell or a virus where it is not normally found in nature; or, comprises two or more subsequences which are not found in the same relationship to each other as normally found in nature, or is recombinantly engineered so that its level of expression, or physical relationship to other nucleic acids or other molecules in a cell, or structure, is not normally found in nature.

For instance, a heterologous nucleic acid is typically recombinantly produced, having two or more sequences from unrelated genes arranged in a manner not found in nature; e.g., a human gene as a transgene operatively linked to a promoter sequence inserted into an adenovirus-based vector of the invention. As another example, the transgene can be a cytotoxin, wherein the adenovirus is administered for the treatment of cancer. Heterologous sequences can comprise various combinations of promoters and sequences (e.g., transgenes), examples of which are described in detail herein.

The term "inverted terminal repeat sequence" or "ITR" refers to the common usage of the term with respect to adenoviruses and includes all ITR sequences and variations thereof that are functionally equivalent, i.e., the term refers to sets of sequences (motifs) which flank (on the right and left) the linear adenovirus genome and are necessary for replication of the adenovirus genomic nucleic acid. The Ad sequences of the vectors and vector systems of the invention are flanked by ITRs. There is a high degree of sequence conservation within the ITR between adenoviruses of different serotypes, see, e.g., Schmid (1995) Current Topic in Microbiol. and Immunol. 199(Pt.1):67–80.

The phrase "lacking the ability to produce a functional adenovirus serotype 52/55 kDa trans-acting protein" means that no 52/55 kDa protein is produced or the 52/55 kDa protein that is produced cannot support the encapsidation of a nucleic acid comprising a cis-acting packaging signal of the same Ad serotype into a complete Ad capsid.

The term "nucleic acid" or "nucleic acid sequence" refers to a deoxyribonucleotide or ribonucleotide oligonucleotide in either single- or double-stranded form. The term encompasses nucleic acids, i.e., oligonucleotides, containing known analogues of natural nucleotides. The term also encompasses nucleic-acid-like structures with synthetic backbones, see e.g., Oligonucleotides and Analogues, a Practical Approach, ed. F. Eckstein, Oxford Univ. Press (1991); Antisense Strategies, Annals of the N.Y. Academy of Sciences, Vol 600, Eds. Baserga et al. (NYAS 1992); Milligan (1993) J. Med. Chem. 36:1923–1937; Antisense Research and Applications (1993, CRC Press), WO 97/03211; WO 96/39154; Mata (1997) Toxicol. Appl. Pharmacol. 144:189–197; Strauss-Soukup (1997) Biochemistry 36:8692–8698; Samstag (1996) Antisense Nucleic Acid Drug Dev 6:153–156.

The phrase "nucleic acid sequence encoding" refers to a nucleic acid comprising sequence that encodes a protein or peptide. It can also include translational or transcriptional regulatory element sequence. The nucleic acid sequence can include both the DNA strand sequence that is transcribed into RNA and the RNA sequence that is translated into protein. The nucleic acid sequences can include degenerate codons of a native sequence or sequences that may be introduced to provide codon preference in a specific host cell.

The term "pharmaceutical composition" refers to a composition suitable for pharmaceutical use in a subject. The pharmaceutical compositions of this invention are formulations that comprise a pharmacologically effective amount of a composition comprising a vector or combination of vectors of the invention (i.e., a vector system) and a pharmaceutically acceptable carrier.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of polypeptide coding sequences in the vectors of invention.

The term "replication deficient" or "replication defective" refers to a viral genome that does not comprise all the genetic information necessary for replication and formation of a genome-containing capsid in a replication competent cell under physiologic (e.g., in vivo) conditions.

The invention provides a pharmaceutical composition comprising an encapsidated replication defective adenovirus substantially free of helper virus. The term "substantially free of helper virus" or "substantially free of replication competent virus" means that less than about 0.01%, 0.02%, 0.03%, 0.05%, 0.1%, 0.2%, 0.3%, 0.4%, 0.5% or about 1.0% of the capsids in a preparation (e.g., the product of an infection by the vector system of the invention) can replicate in a replication competent cell without some form of complementation by another source, such as the cell, another virus, a plasmid, and the like. In alternative embodiments, pharmaceutical compositions are 100% pure, and about 99.99%, 99.98%, 99.97%, 99.96%, 99.95%, 99.93%, 99.90%, 99.5%, 99.0%, 98%, 97%, 95%, 93% and 90% pure of helper virus.

The term "replication competent cell" or "replication competent host cell" or "producer cell" includes any cell capable of supporting the replication of an adenoviral genome and capsid and the encapsidation process. Typically, these cell lines are anchorage dependent viral packaging cell lines. Anchorage dependent cells, or cultures derived from them, are those that will grow, survive, or maintain function optimally when attached to a surface such as glass or plastic. Anchorage dependent cell lines commonly used for mammalian cell culture can be used as viral packaging cell lines. Examples of such anchorage dependent cell lines are HeLa cells; 911 cells (see, e.g., Fallaux (1996) Hum. Gene Ther. 7:215–222); 293 cells (see, e.g., Graham (1977) J. Gen. Virol. 36:59–72) and PER.C6 cells (see, e.g., WO/97/00326).

The term "sufficient adenoviral nucleic acid sequence to encode a viral capsid" means an adenoviral genome comprises sufficient genetic information to form a complete viral capsid in a replication competent cell under physiologic (e.g., in vivo) conditions.

The invention provides pharmaceutical compositions for in vitro and for in vivo systemic, regional and local administration. The term "systemic administration" refers to administration of a composition of the invention, such as the Ad vectors and vector systems of the invention, in a manner that results in the introduction of the composition(s) into the circulatory system. The term "regional administration" refers to administration of a composition into a specific anatomical space, such as intraperitoneal, intrathecal, subdural, or to a specific organ, and the like. For example, regional administration includes administration of the composition into the hepatic artery for regional administration to the liver. The term "local administration" refers to administration of a composition into a limited, or circumscribed, anatomic space, such as intratumoral injection into a tumor mass, subcutaneous injections, intramuscular injections, and the like. Any one of skill in the art would understand that local administration or regional administration also can result in entry of the composition into the circulatory system.

Adenovirus DNA, Genomes and Virions

This invention provides novel engineered adenovirus genomes for use in the production of preparations of replication defective Ad gene transfer vectors that are substantially free of replication competent virus, such as helper virus. As the genes and vectors of the invention can be made and expressed in vitro or in vivo, the invention provides for a variety of means of making and expressing these genes and vectors. One of skill will recognize that desired phenotypes associated with altered gene activity can be obtained by modulating the expression or activity of the genes and nucleic acids (e.g., ITRs, promoters) within the vectors of the invention. Any of the known methods described for increasing or decreasing expression or activity can be used for this invention. The invention can be practiced in conjunction with any method or protocol known in the art, which are well described in the scientific and patent literature.

General Techniques

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to mammalian cells, e.g., bacterial, yeast, insect or plant systems.

Alternatively, these nucleic acids can be synthesized in vitro by well-known chemical synthesis techniques, as described in, e.g., Carruthers (1982) Cold Spring Harbor Symp. Quant. Biol. 47:411–418; Adams (1983) J. Am. Chem. Soc. 105:661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, e.g., generating mutations in sequences, subcloning, labeling probes, sequencing, hybridization and the like are well described in the scientific and patent literature, see, e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Structure and Properties of Adenovirus

Capsid Structure

In the vector system of the invention the first replication defective adenovirus sequence comprising a first Ad serotype cis-acting packaging sequence and a heterologous nucleic acid, flanked by ITRs, can lack some or all of the genetic information necessary to synthesize a capsid structure (described below). The deleted sequences can be completely or partially complemented by the second replication defective adenovirus, an Ad replication-competent cell, a third nucleic acid (e.g., a plasmid or virus), or a combination thereof. In one vector system of the invention, the first replication defective adenovirus sequence is encapsidated in a capsid comprising polypeptides encoded by the second replication defective adenovirus sequence (the "helper virus") when both sequences are expressed in an adenovirus replication-competent host cell.

All adenovirus virions are nonenveloped icosahedral capsids surrounding a linear double stranded DNA genome. Virions are about 80 to 110 nm in diameter with about 252 capsomers each about 8 to 10 nm in diameter. The 240 nonvertex capsomers (hexons) are formed by the interaction of three identical polypeptides. The atomic structure of hexon polypeptide as determined by X-ray crystallography (Roberts (1986) Science 232:1148–1151) indicates that it has two distinct parts: a triangular top with three towers exposed to the environment and bearing type-specific antigenic determinants (Toogood (1992) J. Gen. Virol. 73:1429–1435) and a pseudo hexagonal base with a central cavity. Penton polypeptides form the 12 vertices of the viral icosahedron, a pentamer of penton bases tightly associated with a trimer of fibres projecting from the surface.

Adenovirus Serotypes

The invention provides adenovirus vectors, Ad genes and Ad subsequences derived from all Ad serotypes. The vectors of the invention include genomes and nucleic acid sequences from all of the family Adenoviridae including avian, human and other mammalian strains and serotypes. The family Adenoviridae is currently divided into two genera named *Mastadenovirus* and *Aviadenovirus*. All adenoviruses are morphologically and structurally similar. The human adenoviruses (Ads) belong to the genus *Mastadenovirus*. Human adenoviruses show diverging immunological properties and are divided into serotypes and, to date, 47 distinct serotypes have been identified. These are divided into six subgenera (A to F) on the basis of shared immunological and biochemical properties. Different serotypes are associated with a variety of acute infections, primarily respiratory, ocular, and gastrointestinal. For example, serotypes Ad 40 and Ad 41 can be isolated in high yield from feces of young children with acute gastroenteritis. The invention also includes use of newly isolated serotypes that can be identified using routine screening (see, e.g., Itoh (1999) J. Med. Virol. 59:73–77) or human cell-infecting non-human adenovirus (see, e.g., Rasmussen (1999) Hum Gene Ther. 10:2587–2599, describing canine Ad 2 and bovine Ad 3 infecting human cells).

Many adenovirus serotype genomes have been isolated and characterized (see, e.g., Chroboczek (1992) Virology 186: 280–285, comparing the Ad5 and the Ad2 genomes). For example, in Ad2 the genome is 35,937 base pairs long; see, e.g., Akusjarvi, G. et al. (1986) Structure and function of the adenovirus genome, In Adenovirus DNA, Doerfler, W., Ed., Martinus Nijhoff Publishing, Boston. The complete Ad serotype 17 (Ad 17) genome is described by Chillon (1999) J. Virol. 73 (3), 2537–2540, GenBank accession no. AF108105; for the Ad 40 complete genome see GenBank accession no. L19443; for the Ad 12 complete genome see GenBank accession no. X73487, and the like. See also, e.g., National Library of Medicine, and, Index Virum on the world wide web at life.anu.edu.au/viruses/Ictv/fr-index.htm. For non-human adenoviruses, see, e.g., Reddy (1999) J. Gen. Virol. 80:563–70; Matiz (1999) Virus Res. 55:29–35.

Genetic Engineering of Novel Adenovirus Vectors

The invention provides novel vector systems for serotype-specific, selective packaging (encapsidation) of adenovirus nucleic acid sequences in replication defective virions. The vector systems of the invention produce Ad gene therapy vector preparations that are substantially free of replication competent "helper virus." The vector system comprises two replication defective adenovirus constructs. One of the replication defective adenovirus constructs comprises a first adenovirus serotype cis-acting packaging sequence and a heterologous nucleic acid, flanked by adenovirus inverted terminal repeat (ITR) sequences, lacking the ability to produce a polypeptide having the activity of a first adenovirus serotype 52/55 kDa trans-acting protein. In one embodiment, Ad sequences have been deleted from the Ad genome used to make this vector. In another embodiment, all Ad sequences except for the flanking ITRs and the Ad serotype-specific cis-acting packaging sequence have been deleted.

The second construct comprises a second adenovirus serotype cis-acting packaging sequence, flanked by adenovirus ITR sequences, lacking the ability to produce a polypeptide having the activity of a second adenovirus serotype 52/55 kDa trans-acting protein. In one embodiment, the second "helper virus" construct comprises some or all of the genomic sequence to allow complete capsid synthesis, assembly and packaging (in conjunction with the serotype-matched packaging factors).

The invention also provides a vector for selectively packaging Ad nucleic acid sequences in replication defective virions comprising a replication defective Ad sequence comprising a first Ad serotype cis-acting packaging sequence, a nucleic acid sequence encoding a polypeptide having the activity of a second Ad serotype 52/55 kDa trans-acting protein, and sufficient Ad nucleic acid sequence to encode a viral capsid, flanked by inverted terminal repeat sequences.

To allow for packaging of the heterologous nucleic acid (transgene)-containing construct (with a first serotype specific cis-acting sequence), the vector system includes a nucleic acid sequence encoding a 52/55 kDa trans-acting protein that can functionally complement the first cis-acting packaging signal (to allow for encapsidation). This polypeptide can be inserted into the second "helper virus" construct or it can be expressed in the Ad replication competent cell. In another embodiment, this 52/55 kDa polypeptide-encoding sequence is inserted in the transgene-containing construct having the first cis-acting packaging sequence. In this latter example the packaged virion must be replication defective; thus, it must also lack at least one functional gene or polypeptide needed for replication in a replication competent cell. In one embodiment, all virion genes are deleted or disabled except for the flanking ITRs and the cis-acting packaging signal.

While adenovirus vectors are normally trophic for the respiratory epithelium (Straus, In Adenoviruses, Plenan Press, New York, pp. 451–496 (1984), the capsid proteins can be designed to re-target the gene therapy virus to a variety of different cell types. Chimeric Ad coat proteins, e.g., a fiber, hexon or penton protein (see above), can be so engineered by introduction of a normative amino acid sequence, e.g., at or near the carboxyl terminus. Re-targeting is accomplished by, e.g., recombinantly engineering a heterologous cell targeting ligand into the Ad fiber, hexon or penton receptor gene; see, e.g., Gonzalez (1999) Gene Ther. 6:314–20; U.S. Pat. No. 5,965,541. Examples of such modifications are described in Wickham (1997) J. Virol 71:8221–8229 (incorporation of RGD peptides into adenoviral fiber proteins); Arnberg.(1997) Virology 227:239–244 (modification of adenoviral fiber genes to achieve tropism to the eye and genital tract); Harris (1996) TIG 12:400–405; Stevenson (1997) J. Virol. 71:4782–4790; Michael (1995) Gene Therapy 2:660–668 (incorporation of gastrin releasing peptide fragment into adenovirus fiber protein); and Ohno (1997) Nature Biotechnol. 15:763–767 (incorporation of Protein A-IgG binding domain into Sindbis virus). Other methods of cell specific targeting have been achieved by the conjugation of antibodies or antibody fragments to the envelope proteins (see, e.g. Michael (1993) J. Biol. Chem. 268:6866–6869; Watkins (1997) Gene Therapy 4:1004–1012; Douglas (1996) Nature Biotechnol. 14: 1574–1578. Any protein or other composition can be conjugated to the viral surface to achieve targeting, see, e.g. Nilson (1996) Gene Therapy 3:280–286 (conjugation of EGF to retroviral proteins).

Thus, gene therapy using the pharmaceuticals of the invention can be carried out in the treatment of diseases, disorders, or conditions associated with different tissues that normally lack receptors to which wild-type Ad binds, e.g., for delivery to monocyte/macrophages, fibroblasts, neuronal, smooth muscle, and epithelial cells. Such tissues (and associated diseases, disorders, or conditions) include, e.g., endothelia (e.g., angiogenesis, restenosis, inflammation, and tumors); neuronal tissue (e.g., tumors, chronic pain, Alzheimer's disease); epithelium (e.g., disorders of the skin, cornea, intestine, lung); hematopoietic cells (e.g., human immunodeficiency virus (HIV-1, HIV-2), cancers, anemias); smooth muscle (e.g., restenosis, degeneration, heart disease); fibroblasts (e.g., inflammation, scarring, delayed healing).

Methods to generate and replicate these hybrid constructs are well known in the scientific and patent literature, see, e.g., U.S. Pat. No. 5,981,225; U.S. Pat. No. 5,922,576; U.S. Pat. No. 5,880,102; Graham (1995) Mol. Biotechnol. 3:207–220, and for general methodologies, e.g., Sambrook, Ausubel, Tijssen. Viral genome genetic engineering, transformation and infection techniques in cell culture, viral manipulation and isolation techniques, Ad replication competent cell lines and permissive conditions for Ad replication, and the like, are all well known and described in the scientific and patent literature, see e g., Krougliak (1995) Hum. Gene Ther. 6:1575–1586; Gorziglia (1999) J. Virol. 73:6048–6055; Cote (1998) Biotechnol. Bioeng. 59:567–575; Hartigan-O'Connor (1999) J. Virol. 73:7835–7841; U.S. Pat. No. 5,851,806; U.S. Pat. No. 5,880,102; U.S. Pat. No. 5,882,877; U.S. Pat. No. 5,891,690; U.S. Pat. No. 5,965,541; U.S. Pat. No. 5,981,225; U.S. Pat. No. 5,985,846; U.S. Pat. No. 5,994,106; U.S. Pat. No. 5,955,281.

To make a null mutant in a structural protein (e.g., the 52/55 kDa protein) or a structural motif (e.g., ITR or packaging sequence) base substitutions can be inserted in the open reading frame (ORF), e.g., near the 5' end to create a series of stop codons. Alternatively, complete deletion of genomic sequence can be made (e.g., deletion of genes involved in capsid synthesis, as hexon or penton coding sequences). The engineered ORFs are typically manipulated using both prokaryotic and eukaryotic expression vectors. Manipulated (e.g., mutated or partially deleted) sequences are then inserted back onto an adenovirus chromosome.

Recombinantly engineered adenoviral vectors can be generated by a variety of known procedures, e.g., in vivo homologous recombination method (see, e.g., He (1999) Proc. Natl. Acad. Sci. USA 95:2509–2514; Aoki (1999) Mol. Med. 5:224–231; Souza (1999) Biotechniques 26:502–508; U.S. Pat. No. 5,919,676), by the in vitro direct ligation method (see, e.g., Mizuguchi (1998) Hum. Gene Ther. 9:2577–2583, or using circular adenoviral DNA (see, e.g., Tashiro (1999) Hum. Gene Ther. 10:1845–1852). One exemplary technique, the altered sequences are inserted in a bacterial clone taking advantage of a bacterial recombination system, e.g., as the method described by Chartier (1996) J. Virol 70:4805–4810. This system uses a bacterial plasmid that contains a full length copy of an Ad genome coupled with a simple gene replacement method in E. coli. This allows manipulation of any portion of the Ad genome in a prokaryotic or eukaryotic expression vector followed by insertion into a full length copy of an Ad genome. The full length Ad chromosome is cut once with a restriction enzyme in the region one wishes to replace. Bacteria are co-transformed with this linearized molecule. Homologous recombination yields a circular molecule that is competent for replication in the bacterial cell. Presence of the altered Ad sequence can be confirmed by PCR and Southern blotting.

An encapsidated Ad is produced by transfecting the newly generated, mutated Ad genome into Ad-replication-competent cells, such as, e.g., 293 cell lines. This is followed by incubation, harvesting and plaque purification of the newly produced viruses.

When it is desired to isolate the viral particles from producer cells, the cells are lysed. A variety of means well known in the art can be used. For example, mammalian cells may be lysed under low pressure (100–200 psi differential pressure) conditions or conventional freeze thaw methods. Exogenous free DNA/RNA is removed by degradation with DNAse/RNAse. The viral particles (capsids) are then purified by means known in the art, e.g., chromatographic or differential density gradient. Viral particles can also be purified directly from the initial lysate by, e.g., CsCl density centrifugation, and mature virions collected from the gradient. In one exemplary protocol the treated, buffered cell lysate is first chromatographed over an anion exchange resin followed by chromatography over an immobilized metal affinity resin (see, e.g., U.S. Pat. No. 5,837,520). Anion-exchange high-performance liquid chromatography can also be used (see, e.g., Shabram (1997) Hum. Gene Ther. 8:453–465).

To confirm the genome was packaged (i.e., encapsidated) during the co-infection the lysate can be applied to a new culture of cells. About 48 hours later, viral DNA is isolated and Southern blot analysis is performed to assay for the presence of manipulated Ad sequence. If this sequence had been packaged during the first infection, it will be delivered into the cells during the second infection and amplified. Packaging can also be confirmed by purifying the virus on a density gradient and isolating and analyzing the DNA from the density purified virus. A capsid containing a complete genome can be identified by having a density greater than capsids only containing partial genome or no packaged nucleic acid. After capsid isolation based on density, DNA can be prepared from various capsid samples and analyzed or sequenced.

Growth of Adenovirus in Cell Culture

The vector systems of the invention are used to infect or transform adenovirus replication competent cells, such as 293 cell lines. The primary human embryonic kidney (HEK) 293 cell line is a permanent line of cells transformed by sheared human Ad 5 DNA. The cells are particularly sensitive to human Ad and are highly permissive for Ad DNA. This cell line is readily available from commercial sources, such as the American Type Culture Collection (ATCC CRL 1573). Variants of 293 cell lines can also be used, e.g., see U.S. Pat. No. 5,919,636.

Cells are grown under conditions and for sufficient periods of time to allow production of encapsidated vector. This is typically carried out in a standard cell culture or a bioreactor device for cell culturing. The design of the bioreactor should ensure sterility and provide for containment of the producer cell and recombinant virus. A variety of bioreactors are commercially available for the culture of anchorage dependent producer cells and suspension cultures and are well known to those of skill in the art. Bioreactors can be equipped with an agitation system to keep the contents uniformly mixed and to facilitate oxygen transfer and sensors that permit monitoring and manipulation of various parameters (e.g., temperature, pH, dissolved oxygen) to maintain growth within optimal ranges for cell growth. The cells can be grown in a bioreactor under perfusion conditions. In one exemplary protocol, the Ad replication competent "producer" cells are attached to microcarriers. Serum-free media is frequently used to growth Ad producer cells; this media can be supplemented with hormones such as insulin, transferrin, epidermal growth factor, or hydrocortisone. Serum free media may also be enhanced agents which upregulate or stabilize the viral binding receptors, such as the alpha v beta3 and alpha v beta5 integrins to improve infection efficiency. See, e.g., U.S. Pat. No. 5,994,134.

Characterization and Identification of Cis-Acting Packaging Sequences

The invention provides adenovirus vectors comprising serotype specific cis-acting packaging sequences. Adenoviral genomes without a complete packaging sequence will not be inserted into a capsid structure. In wild type virus, the packaging sequence can contain up to five related domains, called "A repeats." However, the A repeats are not completely functionally redundant; inactivation of individual repeats impairs packaging efficiencies of the resulting mutant viruses to different extents. The packaging sequence from the Ad5 serotype has been reported to be at the genomic left end at about nucleotides 194 to 380 (see Table 1 below). See, e.g., Grable (1990) supra; Grable (1992) supra; Schmid (1995) supra; Schmid (1997) supra; Schmid (1998) supra. Some groups have reported that at least three copies of A repeats are required for efficient DNA encapsidation (see, e.g., Grable (1990) supra; Grable (1992) supra). However, any amount of "A repeat sequence," or "A repeat" efficiency or structural form, or variation of packaging domain sequence can be used in the vectors of the invention as long as they retain their ability to package nucleic acid into a completed Ad capsid in a serotype-matched manner with a 52/55 kDa trans-acting protein.

In wild type adenovirus the packaging signal maps at the left end of the Ad genome. Thus, in the design and construction of the vectors of the invention, this is one location for placement of a packaging sequence. However, in the vectors of the invention the packaging sequence can be placed in any position as long as it retains its ability to package nucleic acid into a completed Ad capsid in a serotype-matched manner with a 52/55 kDa trans-acting protein. For example, it has been noted that neither inversion of the Ad packaging domain nor its relocation to the right end of the genome terminus affected its function; however, it is reported that it must be located within 600 bases of the genomic terminus for proper function (see, e.g., Hammarskjold (1980) Cell 20:787–795; Hearing (1987) J. Virol. 61:2555–2558).

The vectors of the invention can use packaging sequence from any serotype, including the 47 distinct Ad serotypes known to infect humans (see above). Packaging signals can be identified by routine sequence identity and functional analysis, as described below. Identification of a functional packaging sequence from any serotype for use in the vectors of the invention can be routinely identified either by sequence identity (homology) to other serotypes and by functional assays.

For example, packaging region sequence identify between exemplary serotypes (using residue 192 to 400 of Ad5 as an exemplary packaging sequence) is set forth in Table 1, below.

TABLE 1

| Serotype | 3 | 4 | 5 | 7 | 12 | 17 | 40 |
|---|---|---|---|---|---|---|---|
| 3 | 100.0 | 89.2 | 68.1 | 99.0 | 39.5 | 77.2 | 40.4 |
| 4 |  | 100.0 | 70.2 | 89.3 | 51.4 | 78.4 | 40.1 |
| 5 |  |  | 100.0 | 68.3 | 44.5 | 70.3 | 40.4 |
| 7 |  |  |  | 100.0 | 38.8 | 76.2 | 38.7 |
| 12 |  |  |  |  | 100.0 | 34.0 | 45.2 |
| 17 |  |  |  |  |  | 100.0 | 50.0 |
| 40 |  |  |  |  |  |  | 100.0 |

One exemplary assay to identify whether a particular nucleic acid sequence can package nucleic acid into an Ad capsid with a matched trans-acting element is described by Schmid (1997) supra.

Characterization and Identification of 52/55 kDa Polypeptide Encoding Sequences

The invention provides adenovirus vectors comprising serotype specific trans-acting 52/55 kDa polypeptide-encoding sequences. The 52/55 kDa protein must be present in trans with the cis-acting packaging factor in the replication process to form mature virions. See, e.g., Gustin (1998) supra; K. Gustin, Ph.D. Thesis, University of Michigan, supra; Hasson (1989) J. Virol. 63:3612–3621.

The vectors of the invention can use 52/55 kDa protein-encoding sequence from any serotype, including the 47 distinct Ad serotypes known to infect humans. 52/55 kDa protein-encoding sequence can be identified by routine sequence identity to known (human or non-human) 52/55 kDa sequences, by functional analysis (as described below), and other known methods. Several 52/55 kDa protein encoding sequences are known, see, e.g., Genbank accession numbers: for Ad5 P04496; for Ad2: P03262; for Ad12: P36715; for Ad40: AAC13960; for Bovine Ad: AAD09721; for mouse Ad: AAB53752; for canine Ad: Q65948; for Fowl Ad: AAC54906; for ovine Ad AAA84973. Additional assays to identify whether a particular nucleic acid sequence encodes a functional, serotype specific 52/55 kDa polypeptide are described by, e.g., Gustin (1998) supra; K. Gustin, Ph.D. Thesis, University of Michigan, supra.

These routine assays are also used to determine if a 52/55 kDa polypeptide from one serotype can or cannot complement the encapsidation function of the cis-acting packaging sequence of another serotype. The invention is based on the new finding that a cis-acting packaging signal must be serotype matched with a trans-acting 52/55 kDa polypeptide. Typically, the cis- and trans-acting factors are from the same serotype. For example, an Ad5 cis-acting packaging sequence will be complemented by an Ad5 a trans-acting 52/55 kDa polypeptide but not (to a significant degree) by an Ad7 a trans-acting 52/55 kDa polypeptide. Thus, one exemplary vector system of the invention includes a gene therapy vector with an Ad7 cis-acting packaging signal and a helper virus with an Ad5 cis-acting packaging signal, with the system complemented by only an Ad7 a trans-acting 52/55 kDa polypeptide. However, as discussed above, a trans-acting 52/55 kDa polypeptide from another serotype may also be able to significantly complement the Ad5 cis-acting sequence. As long as the trans-acting factor from the third serotype cannot also complement (to a significant degree) the cis-acting sequence in the helper virus (the Ad7 cis-acting sequence in this example), it can be incorporated into the vector system of the invention. Thus, the vectors systems of the invention incorporate any polypeptide which has the serotype-specific activity of the desired a trans-acting 52/55 kDa polypeptide.

In addition to the functional (encapsidation) assays, in vitro and cell-based in vivo assay systems can be used to screen for such the serotype-specific encapsidation activity, including, e.g., cis-acting packaging signal binding proteins. Relevant trans-acting factors from different serotypes can be identified in this manner. Many assays are available that screen for nucleic acid binding proteins and all can be adapted and used with for cis-acting packaging signals from various serotypes. For example, one means to identify a cis-acting packaging signal binding compound is by contacting a cis-acting sequence with a test compound and measuring the ability of the test compound to bind the selected nucleic acid. The test compound can be any agent capable of specifically binding to a cis-acting sequence, including compounds available in chemical (e.g., combinatorial) libraries, a cell extract, a nuclear extract, a protein or peptide. A variety of well-known techniques can be used to identify polypeptides which specifically bind to cis-acting sequences, e.g., mobility shift DNA-binding assays, methylation and uracil interference assays, DNase and hydroxy radical footprinting analysis, fluorescence polarization, and UV crosslinking or chemical cross-linkers. For a general overview, see, e.g., Ausubel (chapter 12, DNA-Protein Interactions). One technique for isolating co-associating proteins, including nucleic acid and DNA/RNA binding proteins, includes use of UV crosslinking or chemical cross-linkers, including e.g., cleavable cross-linkers dithiobis (succinimidylpropionate) and 3,3'-dithiobis (sulfosuccinimidyl-propionate); see, e.g., McLaughlin (1996) Am. J. Hum. Genet. 59:561–569; Tang (1996) Biochemistry 35:8216–8225; Lingner (1996) Proc. Natl. Acad. Sci. USA 93:10712; Chodosh (1986) Mol. Cell. Biol 6:4723–4733. Alternatively, cis-acting sequence-affinity columns can be generated to screen for potential binding proteins. In a variation of this assay, cis-acting sequence are biotinylated, reacted with a solution suspected of containing a binding protein, and then reacted with a strepavidin affinity column to isolate the nucleic acid or binding protein complex (see, e.g., Grabowski (1986) Science 233:1294–1299; Chodosh (1986) supra). The cis-acting sequence-binding protein can then be conventionally eluted and isolated. Mobility shift DNA-protein binding assay using nondenaturing polyacrylamide gel electrophoresis (PAGE) is an extremely rapid and sensitive method for detecting specific polypeptide binding to DNA (see, e.g., Chodosh (1986) supra, Carthew (1985) Cell 43:439–448; Trejo (1997) J. Biol. Chem. 272:27411–27421; Bayliss (1997) Nucleic Acids Res. 25:3984–3990). Interference assays and DNase and hydroxy radical footprinting can also be used to identify specific residues in the nucleic acid protein-binding site, see, e.g., Bi (1997) J. Biol. Chem. 272:26562–26572; Karaoglu (1991) Nucleic Acids Res. 19:5293–5300. Fluorescence polarization is a powerful technique for characterizing macromolecular associations and can provide equilibrium determinations of protein-DNA and protein—protein interactions. This technique is particularly useful (and better suited than electrophoretic methods) to study low affinity protein—protein interactions, see, e.g., Lundblad (1996) Mol. Endocrinol. 10:607–612.

Proteins identified by these techniques can be further separated on the basis of their size, net surface charge, hydrophobicity and affinity for other ligands. In addition, antibodies raised against such proteins can be conjugated to column matrices and the proteins immunopurified. All of these general methods are well known in the art. See, e.g, Scopes, R. K., Protein Purification: Principles and Practice, 2nd ed., Springer Verlag, (1987).

Heterologous Nucleic Acids

The invention provides a replication defective adenovirus sequence comprising an Ad serotype-specific cis-acting packaging sequence and a heterologous nucleic acid, flanked by ITR sequences. The heterologous nucleic acid, as defined above, can comprise any non-viral nucleic acid sequence. When the heterologous nucleic acid is intended for in vivo administration, it can be designed, e.g., to encode therapeutic polypeptides or antisense sequences, such as cell toxins or apoptosis inducing agents to ablate specific cell targets, e.g., cancer cells.

Any size of heterologous nucleic acid can be used in place of wild type sequence. The adenoviral genome, which is a linear, double-stranded DNA, can be manipulated to accommodate heterologous (e.g., non-viral) genes that range in size, including reasonably large DNA inserts to about 38 kilobases (Bett (1993) J. Virol. 67:5911–5921). However, some upper and lower size limits may be necessary to effect packaging of the vector into an Ad capsid. Thus, as a general guideline, an upper limit for total vector size is about 105% of Ad wild type genomic length (see, e.g., Ghosh-Choudhury (1987) EMBO J. 6:1733–1739; Bett (1993) supra). Lower limits for total vector size have been suggested, see, e.g., Mitani (1995) Proc. Natl. Acad. Sci. USA 92:3854–3858. See also Alemany (1997) supra. It has been reported that a preferable total size of the DNA inserted into the Ad vector be is about 28 to 32 kilobases, possibly because Ad needs to have a minimum size to be stably propagated (Parks (1997) J. Virol. 71:3293–3298). If a "gutted" gene transfer vector is used (i.e., most or all of the Ad genes are deleted, as discussed above) and the size of the resulting vector, including heterologous gene insert, ITR, cis-acting packaging sequence and other sequences (e.g., promoters, cell specific enhancer sequences, hormone responsive elements, mammalian artificial chromosome elements or elements from autonomous replicating circular minichromosomes, and the like) is less than about 28–32 kb, it may preferable to include "stuffer DNA". For example, the stuffer DNA may be DNA derived from prokaryotic or eukaryotic genomic noncoding regions. For pharmaceutical compositions, the stuffer DNA can be derived from noncoding human genomic DNA. It has also been reported that Ad vectors with a matrix association region (MAR) have higher expression levels (Sykes (1988) Mol. Gen. Genet. 212:301–309). Inclusion of a MAR sequence in the vector is believed to confer nuclear stability to the vector.

Heterologous nucleic acids can be operably linked to transcriptional control sequences, e.g., promoters, enhancers. Control sequences can comprise Ad sequences normally associated with wild-type Ad genome (e.g., adenovirus major late promoter, Ad MLP). Alternatively, heterologous control sequences can be employed where desired. Useful heterologous promoter sequences include those derived from sequences encoding mammalian genes or viral genes, e.g., the SV40 early promoter, mouse mammary tumor virus LTR (MMTV LTR) promoter, a herpes simplex virus (HSV) promoter, a cytomegalovirus (CMV) promoter (e.g., the CMV immediate early promoter region), a Rous sarcoma virus (RSV) promoter, synthetic promoters, hybrid promoters, and the like. The vectors of the present invention can include selectable markers to, e.g., confer antibiotic resistance or sensitivity, impart color, change the antigenic characteristics when cells which have been transfected are grown in a selective medium. Selectable marker genes include, e.g., neomycin resistance gene (encoding aminoglycoside phosphotransferase) that allows selection in mammalian cells by conferring resistance to G418; the hygromycin-B resistance gene (encoding Hygromycin-B-phosphotransferase).

Exemplary heterologous nucleic acids used as transgenes in the vectors of the invention include, e.g., tumor suppressor genes, cyclin dependent kinase inhibitors, cytotoxic genes, cytostatic genes, proapoptotic genes, prodrug activating genes, tumor specific antigens, or antisense sequences. Examples of tumor suppressor genes include the retinoblastoma (Rb) gene and its variants Rb110 and Rb56, the MMAC-1 gene, the p53 gene, the DCC gene, the NF-1 gene, p33, and p73. Cyclin dependent kinase inhibitors include, e.g., p27kip, p57kip2, p15ink4b, p18ink4c, p19ink4d, p16ink4a and p21sdi-1 genes. Cytotoxic genes are designed to have a toxic effect in the target cell, either alone or in conjunction with exogenous chemical agents (e.g. pro-drug activating genes). Examples include the cytotoxic domains of ricin, diphtheria, or *Pseudomonas* exotoxin as well as the adenovirus E311.6 gene, adenovirus E1a. Examples of pro-drug activating genes include the thymidine kinase and cytosine deaminase genes. Pro-apoptotic genes includes p53 and p53 pathway genes (e.g. bax, bid, caspases, cytochrome C, etc.) and adenovirus E4. Examples of other therapeutic transgenes that can be incorporated into the vectors of the invention include, e.g., interferons (alpha, beta, gamma and consensus), interleukins (e.g. IL-2, IL-4, L-10), or neurotransmitters (e.g., dopamine, serotonin, GABA, ACTH, NGF). In neuromuscular diseases, such as ALS or spinal cord injuries, a heterologous gene can be delivered by Ad vector to prevent cell death and promote survival. For example, adenovirus vectors containing a neurotrophin-3 gene can targeted delivery of NT-3 to motoneurons to treat ALS (see, e.g., Hasse (1998) J. Neurol. Sci. 160 Suppl 1:S97–105). Ad vectors can also be used to replace the mutated Duchenne muscular dystrophy gene (see, e.g., Hoffman (1999) Arch. Pathol. Lab. Med. 123:1050–1052). Ad vectors can be used to treat cystic fibrosis; the CFTR gene can correct defective Cl-transport in well-differentiated epithelial cultures established from human cystic fibrosis (CF) donors (see, e.g., Romanczuk (1999) Hum. Gene Ther. 10:2615–2626).

Formulation and Administration Pharmaceuticals

The invention also provides adenovirus vectors formulated as pharmaceuticals for the transfer of nucleic acids into cells in vitro or in vivo. In addition to dividing cells, adenovirus can be used to infect resting and nondividing cells, such as, e.g., dendritic cells and neurons (see, e.g., Zhong (1999) Eur. J. Immunol. 29:964–72; Miyaguchi (1999) Neuroreport 10:2349–2353); epicardial and pericardial tissue of a patient's heart (see, e.g., U.S. Pat. No. 5,797,870), and others. The vectors, vector systems and methods of the invention can be used to produce replication defective gene transfer and gene therapy vectors, particularly to transfer nucleic acids to human cells in vivo and in vitro. Using the vector system and methods of the invention, these sequences can be packaged as adenovirus gene therapy vector preparations that are substantially free of helper virus and used as pharmaceuticals in, e.g., gene replacement therapy (in somatic cells or germ tissues) or cancer treatment; see, e.g., Karpati (1999) Muscle Nerve 16:1141–1153; Crystal (1999) Cancer Chemother. Pharmacol. 43 Suppl:S90-9.

The vectors, vector systems, pharmaceutical compositions and methods of the invention can also be used in non-human systems. For example, human Ad 5 can be used in gene delivery in laboratory animals (e.g., mice, rats) as well as economically important animals (e.g., swine, cattle); see, e.g., Mayr (1999) Virology 263:496–506; Mittal (1996) Virology 222:299–309; Prevec (1990) J. Infect. Dis. 161:27–30.

These pharmaceuticals can be administered by any means in any appropriate formulation. Routine means to determine drug regimens and formulations to practice the methods of the invention are well described in the patent and scientific literature, and some illustrative examples are set forth below. For example, details on techniques for formulation, dosages, administration and the like are well described in the scientific and patent literature, see, e.g., the latest edition of Remington's Pharmaceutical Sciences, Maack Publishing Co, Easton Pa.

Pharmaceutical Compositions

The invention provides a replication defective adenovirus preparation substantially free of helper virus with a pharmaceutically acceptable carrier (excipient) to form a pharmacological composition. The pharmaceutical composition of the invention can further comprise other active agents, including other recombinant viruses, plasmids, naked DNA or pharmaceuticals (e.g., anticancer agents).

Pharmaceutically acceptable carriers can contain a physiologically acceptable compound that acts, e.g., to stabilize the composition or to increase or decrease the absorption of the agent and/or pharmaceutical composition. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of any co-administered agents, or excipients or other stabilizers and/or buffers. Detergents can also used to stabilize the composition or to increase or decrease the absorption of the pharmaceutical composition (see infra for exemplary detergents).

Other physiologically acceptable compounds include wetting agents, emulsifying agents, dispersing agents or preservatives that are particularly useful for preventing the growth or action of microorganisms. Various preservatives are well known, e.g., ascorbic acid. One skilled in the art would appreciate that the choice of a pharmaceutically acceptable carrier, including a physiologically acceptable compound depends, e.g., on the route of administration of the adenoviral preparation and on the particular physio-chemical characteristics of any co-administered agent.

The compositions for administration will commonly comprise a buffered solution comprising adenovirus in a pharmaceutically acceptable carrier, e.g., an aqueous carrier. A variety of carriers can be used, e.g., buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of capsids in these formulations can vary widely, and will be selected primarily based on fluid volumes, viscosities, body weight and the like in accordance with the particular mode of administration selected and the patient's needs.

Determining Dosing Regimens

The pharmaceutical formulations of the invention can be administered in a variety of unit dosage forms, depending upon the particular condition or disease, the general medical condition of each patient, the method of administration, and the like. In one embodiment, the concentration of capsids in the pharmaceutically acceptable excipient is between about $10^3$ to about $10^{18}$ or between about $10^5$ to about $10^{15}$ or between about $10^6$ to about $10^{13}$ particles per mL in an aqueous solution. Details on dosages are well described in the scientific and patent literature, see, e.g., the latest edition of Remington's Pharmaceutical Sciences; Sterman (1998) Hum. Gene Ther. 9:1083–1092; Smith (1997) Hum. Gene Ther. 8:943–954.

The exact amount and concentration of virus and the amount of formulation in a given dose, or the "therapeutically effective dose" is determined by the clinician, as discussed above. The dosage schedule, i.e., the "dosing regimen," will depend upon a variety of factors, e.g., the stage and severity of the disease or condition to be treated by the gene therapy vector, and the general state of the patient's health, physical status, age and the like. The state of the art allows the clinician to determine the dosage regimen for each individual patient and, if appropriate, concurrent disease or condition treated. Adenovirus has been safely used for many years for human vaccines; see, e.g., Horwitz (1990) supra; Straus (1984) supra; Haj-Ahmad (1986) *J. Virol.*, 57:267); Ballay (1985) *EMBO*, 4,3861 (1985); PCT patent application WO 94/17832). Human adenoviruses have been used in humans as in vivo gene delivery vehicles (Graham & Prevec in *New Approaches to Immunological Problems*, Ellis (ed), Butterworth-Heinemann, Boston, Mass., pp. 363–390 (1992); Ragot (1993) *Nature* 361:647–650 (1993); Kozarsky (1993) *Curr. Opin. Genet. Dev.* 3:499–503); U.S. Pat. No. 5,981,225. These illustrative examples can also be used as guidance to determine the dosage regiment, i.e., dose schedule and dosage levels administered when practicing the methods of the invention.

Single or multiple intrathecal administrations of adenoviral formulation can be administered, depending on the dosage and frequency as required and tolerated by the patient. Thus, one typical dosage for regional (e.g., IP or intrathecal) administration is between about 0.5 to about 50 mL of a formulation with about $10^{13}$ viral particles per mL. In an alternative embodiment, dosages are from about 5 mL to about 20 mL are used of a formulation with about $10^9$ viral particles per mL. Lower dosages can be used, such as is between about 1 mL to about 5 mL of a formulation with about $10^6$ viral particles per mL. Based on objective and subjective criteria, as discussed herein, any dosage can be used as required and tolerated by the patient.

The exact concentration of virus, the amount of formulation, and the frequency of administration can also be adjusted depending on the levels of in vivo (e.g., in situ) transgene expression and vector retention after an initial administration.

Routes of Delivery

The pharmaceutical compositions of the invention can be delivered by any means known in the art systemically (e.g., intravenously), regionally, or locally (e.g., intra- or peritumoral or intracystic injection, e.g., to treat bladder cancer) by, e.g., intraarterial, intratumoral, intravenous (IV), parenteral, intra-pleural cavity, topical, oral, or local administration, as subcutaneous, intra-tracheal (e.g., by aerosol) or transmucosal (e.g., buccal, bladder, vaginal, uterine, rectal, nasal mucosa), intra-tumoral (e.g., transdermal application or local injection). For example, intra-arterial injections can be used to have a "regional effect," e.g., to focus on a specific organ (e.g., brain, liver, spleen, lungs). For example, intra-hepatic artery injection can be used if the anti-tumor regional effect is desired in the liver; or, intra-carotid artery injection. If it is desired to deliver the viral preparation to the brain, (e.g., for treatment of brain tumors), it is injected into a carotid artery or an artery of the carotid system of arteries (e.g., occipital artery, auricular artery, temporal artery, cerebral artery, maxillary artery, etc.).

The vectors of the present invention, alone or in combination with other suitable components can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations such as in a nebulizer or an atomizer. Typically such administration is in an aqueous pharmacologically acceptable buffer as described above. Delivery to the lung can be also accomplished, e.g., by use of a bronchoscope. Gene therapy to the lung includes, e.g., gene replacement therapy for cystic fibrosis (using the cystic fibrosis transmembrane regulator gene) or for treatment of lung cancers or other respiratory conditions.

Additionally, the vectors employed in the present invention may be made into suppositories by mixing with a variety of bases such as emulsifying bases or water-soluble bases. Formulations suitable for vaginal administration may be presented as pessaries, tampons, creams, gels, pastes, foams, or spray formulas.

The pharmaceutical formulations of the invention can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The adenoviral constructs can also be administered in a lipid formulation, more particularly either complexed with liposomes to for lipid/nucleic acid complexes (e.g., as described by Debs and Zhu (1993) WO 93/24640; Mannino (1988) supra; Rose, U.S. Pat. No. 5,279,833; Brigham (1991) WO 91/06309; and Felgner (1987) supra) or encapsulated in liposomes, as in immunoliposomes directed to specific tumor markers. It will be appreciated that such lipid formulations can also be administered topically, systemically, or delivered via aerosol.

Kits

The invention provides kits that contain the vectors, vector systems or pharmaceutical compositions of the invention. The kits can also contain adenovirus replication-competent cells, such as 293 cells. The kit can contain instructional material teaching methodologies, e.g., means to isolate replication defective transgene containing adenovirus. Kits containing pharmaceutical preparations can include directions as to indications, dosages, routes and methods of administration, and the like.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following example is offered to illustrate, but not to limit the claimed invention.

Example 1

Selective Packaging of Adenovirus Genome by Serotype Matching and Mismatching of Cis- and Trans-Acting Packaging Factors The following example demonstrates that the compositions and methods of the invention can be used to produce replication defective adenovirus vector preparations that are substantially free of replication competent "helper" virus. These novel compositions and methods are based on the finding that interaction between Ad cis-acting packaging regions and Ad trans-acting 52/55 kDa protein must be serotype matched to produce an encapsidated adenovirus. Typically, a 52/55 kDa protein from a given serotype is only able to support encapsidation in conjunction with a packaging sequence from that same serotype.

In these experiments an adenovirus serotype 5 (Ad5) deletion mutant (specifically mutated in the 52/55 kDa polypeptide encoding region, called "pm8001") was complemented in trans using 52/55 kDa proteins from a matching serotype. Adding the (serotype matched) Ad5 52/55 kDa protein in trans with pm8001 under replication permissive conditions allowed packaging of nucleic acid comprising Ad5 packaging sequence. However, 52/55 kDa protein from a different serotype (Ad7) could not complement the pm8001 mutation.

Construction of a 52/55 kDa Protein Defective Adenovirus

To make a null mutant in the 52/55 kDa protein, base substitutions near the 5' end of the 52/55 kDa open reading frame were made to create a series of stop codons. FIG. 1 shows the sequence of the N-terminus of the Ad5 52/55 kilodalton protein open reading frame (ORF) in upper case letters; directly below is the corresponding amino acid sequence. Below that in lower case are the point mutations that introduce a series of stop codons, indicated by asterisks.

Ad5 52/55 kilodalton protein ORFs with these mutations were built into both prokaryotic and eukaryotic expression vectors. It was confirmed that none of these vectors express any 52/55 kDa protein. The mutated sequence was then inserted back onto an adenovirus chromosome in a bacterial clone taking advantage of a bacterial recombination system as described by Chartier (1996) J. Virol 70:4805–4810. This system uses a bacterial plasmid that contains a full length copy of the Ad5 genome coupled with a simple gene replacement method in E. coli. This allows mutation of any portion of the adenoviral genome in a prokaryotic or eukaryotic expression vector followed by insertion of the mutation into a full length copy of the Ad5 genome. The adenovirus chromosome was cut once with a restriction enzyme in the region one wishes to replace. This was used to co-transform bacteria with a linear DNA molecule containing the engineered mutation. Homologous recombination yielded a circular molecule that was competent for replication in the bacterial cell. Presence of the mutation was confirmed by PCR and Southern blotting. A linear adenovirus was produced by transfecting the viral newly generated, mutated adenoviral genome into 293-L1 cells (293 cells that stably express the Ad5 52/55 kDa protein, see, Gustin (1998) J. Virol. 72:7860–7870) and incubation followed by harvesting and plaque purifying the newly produced viruses. This new 52/55 kilodalton protein null Ad5 virus mutant was designated "pm8001."

The most striking phenotype of pm8001 virus was that it forms full length Ad genomes and fully formed, but empty, capsids (i.e., only protein, no inserted nucleic acid) in replication competent cells. The pm8001 mutant strain shows no packaging of nucleic acid into its capsids at all.

Complementation Experiments

Experiments showed that pm8001 can grow in 293 cells that constitutively express the wildtype Ad5 52/55 kilodalton protein but not in 293 cells alone or in cells complemented with a non-matching (Ad7) 52/55 kilodalton protein. Cells were infected with pm8001 alone, full length wildtype (wt) Ad5 alone, full length wt Ad7 alone, pm8001 plus Ad5, or pm8001 plus Ad7 using standard procedures. An additional control was to infect 293-L1 cells, which express the Ad5 52/55 kDa protein constitutively, with pm8001.

After 24 to 48 hours, enough time for the virus to complete its replication cycle, a viral lysate is prepared. Two approaches were taken to determine if the pm8001 genome was packaged (i.e., encapsidated) during the co-infection. In one approach, this lysate is applied to a new culture of 293 cells. 48 hours later, viral DNA is isolated and Southern blot analysis is performed to assay for the presence of pm8001 DNA. If this DNA had been packaged during the first infection, it will be delivered into the cells during the second infection and amplified. In the second approach, viral particles (capsids) are purified directly from the initial lysate by CsCl density centrifugation. Mature virion capsids are collected from the gradient. Capsids with full length Ad genomes will have greater densities than those with only partial genomes or no packaged nucleic acid. DNA is also prepared from these particles and assayed for the presence of pm8001 genomes.

DNA was extracted and digested with KpnI and SpeI, and Southern blot analysis performed. The mutation in pm8001 introduces an additional SpeI site into the Ad5 genome. Therefore, one of the higher MW restriction digest products (a "band" in a gel) that is present in the Ad5 digest sample is lost in the pm8001 digest with the concomitant appearance of two additional lower MW bands. The latter two bands are only present after Spe I digestion of the pm8001 genome (not the wt Ad5). Neither of these two bands (nor any of the other Ad5/pm8001-specific bands) were present in capsids generated from the wt Ad7 plus pm8001 co-transfected sample. Thus, wt Ad7 52/55 kDa protein could not substitute for the Ad5 protein and allow for (i.e., complement) packaging of the pm8001 genome.

These findings demonstrate that the cis- and trans-acting elements of the adenovirus genome packaging system must be serotype matched to produce a packaged adenoviral genome. Thus, the vector systems of the invention comprising adenoviral vectors with mismatched cis-acting packaging signals can be used to produce replication defective vector preparations (e.g., pharmaceuticals) substantially free of replication competent "helper" virus.

What is claimed is:

1. A vector system for selectively packaging a replication defective adenovirus nucleic acid sequence in an adenovirus capsid based on adenovirus serotype, the vector system comprising:
   (a) a first adenovirus nucleic acid sequence comprising:
      (i) 5' and 3' adenovirus inverted terminal repeats (ITRs);
      (ii) a first adenovirus serotype-specific cis-acting packaging sequence; and
      (iii) a heterologous nucleic acid operably linked to a transcriptional control sequence;
   wherein the first adenovirus nucleic acid sequence comprises a defective or modified adenovirus E1 gene, E2A gene, E2B gene, E3 gene, E4 gene, E4 promoter, penton gene, fiber gene, hexon gene, or a combination thereof, and wherein the first adenovirus nucleic acid fails to encode a 52/55 kDa trans-acting protein specific for the first cis-acting packing sequence;
   (b) a second adenovirus nucleic acid sequence comprising:
      (i) 5' and 3' adenovirus ITRs;
      (ii) a second adenovirus serotype-specific cis-acting packaging sequence; and
      wherein the second adenovirus nucleic acid sequence complements the defective or modified adenovirus E1 gene, E2A gene, E2B gene, E3 gene, E4 gene, E4 promoter, penton gene, fiber gene, hexon gene, or a combination thereof of the first adenovirus nucleic acid sequence, and wherein the second adenovirus nucleic acid fails to encode a 52/55 kDa trans acting protein specific for the second cis-acting packing sequence;
   (c) an adenovirus replication competent host cell comprising a nucleic acid sequence encoding an adenovirus 52/55 kDa trans-acting protein that supports packaging of the first adenovirus nucleic acid sequence and fails to support packaging of the second adenovirus nucleic acid sequence,
   wherein the replication defective adenovirus comprises the first adenovirus nucleic acid sequence.

2. The vector system of claim 1, wherein the adenovirus capsid and 52/55 kDa protein are from human adenovirus and wherein the first and second adenovirus nucleic acid sequences are from human adenovirus.

3. The vector system of claim 1, wherein the first and second adenovirus serotype-specific cis-acting packaging sequences are selected from the group consisting of adenovirus type 2 (Ad2), adenovirus type 5 (Ad5), adenovirus type 7 (Ad7), adenovirus type 12 (Ad12), adenovirus type 17 (Ad17), and adenovirus type 40 (Ad40) packaging sequences, and wherein the first serotype-specific cis-acting packaging sequence is from a different serotype than the second adenovirus serotype-specific cis-acting packaging sequence.

4. The vector system of claim 3, wherein the first adenovirus serotype-specific cis-acting packaging sequence is from adenovirus type 5 and the second adenovirus serotype-specific cis-acting packaging sequence is from adenovirus type 7.

5. The vector system of claim 3, wherein the first adenovirus serotype-specific cis-acting packaging sequence is from adenovirus type 7 and the second adenovirus serotype-specific cis-acting packaging sequence is from adenovirus type 5.

6. The vector system of claim 1, wherein the failure to encode a functional 52/55 kDa trans-acting protein is due to a mutation in the sequence encoding the protein.

7. The vector system of claim 6, wherein the mutation is a missense mutation, a point mutation, a frameshift mutation or a deletion mutation.

8. The vector system of claim 1, wherein the nucleic acid sequence encoding an adenovirus 52/55 kDa trans-acting protein that supports packaging of the first adenovirus nucleic acid sequence is encoded by a nucleic acid sequence functionally-associated with the genome of the adenovirus replication competent host cell containing the vector system.

9. The vector system of claim 8, wherein the adenovirus replication competent host cell is a 293 cell line.

10. A vector system for selectively packaging a replication defective adenovirus nucleic acid sequence in an adenovirus capsid based on adenovirus serotype, the vector system comprising:
    (a) a first adenovirus nucleic acid sequence comprising:
       (i) 5' and 3' adenovirus ITRS;
       (ii) a first adenovirus serotype-specific cis-acting packaging sequence; and
       (iii) a heterologous nucleic acid operably linked to a transcriptional control sequence;
       wherein the first adenovirus nucleic acid sequence comprises a defective or modified adenovirus E1 gene, E2A gene, E2B gene, E3 gene, E4 gene, E4 promoter, penton gene, fiber gene, hexon gene, or a combination thereof, and wherein the first adenovirus nucleic acid fails to encode a 52/55 kDa trans-acting protein specific for the first cis-acting packing sequence;
    (b) a second adenovirus nucleic acid sequence comprising:
       (i) 5' and 3' adenovirus ITRs;
       (ii) a second adenovirus serotype-specific cis-acting packaging sequence;
       (iii) a nucleic acid sequence encoding an adenovirus 52/55 kDa trans-acting protein that supports packaging of the first adenovirus nucleic acid sequence and fails to support packaging of the second adenovirus nucleic acid sequence;
       wherein the second adenovirus nucleic acid sequence complements the defective or modified adenovirus E1 gene, E2A gene, E2B gene, E3 gene, E4 gene, E4 promoter, penton gene, fiber gene, hexon gene, or a combination thereof of the first adenovirus nucleic acid sequence; and
    (c) an adenovirus replication competent host cell;
       wherein the replication defective adenovirus comprises the first adenovirus nucleic acid sequence.

11. A vector comprising a replication defective adenovirus sequence comprising:
    (a) a first adenovirus serotype-specific cis-acting packaging sequence; and
    (b) a nucleic acid sequence encoding a functional adenovirus serotype-specific 52/55 kDa protein, wherein said protein is specific for a second adenovirus serotype specific cis-acting packaging sequence and is not specific for the first adenovirus serotype-specific cis acting packaging sequence,
    wherein the replication defective adenovirus sequence comprises a defective or modified adenovirus E1 gene, E2A gene, E2B gene, E3 gene, E4 gene, E4 promoter, penton gene, fiber gene, hexon gene, or a combination thereof.

12. The vector of claim 11, further comprising at least one adenoviral nucleic acid sequence needed to produce an adenoviral capsid.

13. The vector of claim 12, further comprising sufficient adenoviral nucleic acid sequence to encode a complete adenoviral capsid when the vector is expressed in an adenovirus replication-competent host cell.

14. The vector of claim 11, wherein the first adenovirus serotype specific cis-acting packaging sequence and second adenovirus serotype-specific sequence are selected from an adenovirus from the group consisting of adenovirus type 2 (Ad2), adenovirus type 5 (Ad5), adenovirus type 7 (Ad7), adenovirus type 12 (Ad12), adenovirus type 17 (Ad17), and adenovirus type 40), and wherein the first serotype-specific cis-acting packaging sequence is from an adenovirus of a different serotype than the second adenovirus serotype-specific cis-acting packaging sequence.

15. The vector of claim 14, wherein the first adenovirus serotype sequence is from adenovirus type 5 and the second adenovirus serotype sequence is from adenovirus type 7.

16. The vector of claim 14, wherein the first adenovirus serotype sequence is from adenovirus type 7 and the second adenovirus serotype sequence is from adenovirus type 5.

17. A transformed or isolated infected cell comprising the vector of claim 11.

18. A kit useful for producing encapsidated adenovirus replication defective nucleic acid sequences, the kit comprising:
(a) a container containing a first adenovirus nucleic acid sequence comprising:
  (i) 5' and 3' adenovirus inverted terminal repeats (ITRs);
  (ii) a first adenovirus serotype-specific cis-acting packaging sequence; and
  (iii) a heterologous nucleic acid operably linked to a transcriptional control sequence;
  wherein the first adenovirus nucleic acid sequence comprises a defective or modified adenovirus E1 gene, E2A gene, E2B gene, E3 gene, E4 gene, E4 promoter, penton gene, fiber gene, hexon gene, or a combination thereof, and wherein the first adenovirus nucleic acid fails to encode a 52/55 kDa trans-acting protein specific for the first cis-acting packing sequence;
(b) a container containing a second adenovirus nucleic acid sequence comprising:
  (i) 5' and 3' adenovirus ITRs;
  (ii) a second adenovirus serotype-specific cis-acting packaging sequence; and wherein the second adenovirus nucleic acid sequence complements the defective or modified adenovirus E1 gene, E2A gene, E2B gene, E3 gene, E4 gene, E4 promoter, penton gene, fiber gene, hexon gene, or a combination thereof of the first adenovirus nucleic acid sequence, and wherein the second adenovirus nucleic acid fails to encode a 52/55 kDa trans acting protein specific for the second cis-acting packing sequence;
(c) a container containing an adenovirus replication competent host cell comprising a nucleic acid sequence encoding an adenovirus 52/55 kDa trans-acting protein that supports packaging of the first adenovirus nucleic acid sequence and fails to support packaging of the second adenovirus nucleic acid sequence,
wherein the replication defective adenovirus comprises the first adenovirus nucleic acid sequence.

19. A method of producing an encapsidated a replication defective adenovirus vector, comprising:
(a) transforming or infecting adenovirus replication competent host cells with
  (i) a first adenovirus nucleic acid sequence comprising:
    5' and 3' adenovirus inverted terminal repeats (ITRs);
    a first adenovirus serotype-specific cis-acting packaging sequence; and
    a heterologous gene operably linked to a transcriptional control sequence,
    wherein the first adenovirus nucleic acid sequence comprises a defective or modified adenovirus E1 gene, E2A gene, E2B gene, E3 gene, E4 gene, E4 promoter, penton gene, fiber gene, hexon gene, or a combination thereof, and wherein the first adenovirus nucleic acid fails to encode a 52/55 kDa trans-acting protein specific for the first cis-acting packing sequence;
  (ii) a second adenovirus nucleic acid sequence comprising:
    5' and 3' adenovirus ITRS;
    a second adenovirus serotype-specific cis-acting packaging sequence,
    wherein the second adenovirus nucleic acid sequence complements the defective or modified adenovirus E1 gene, E2A gene, E2B gene, E3 gene, E4 gene, E4 promoter, penton gene, fiber gene, hexon gene, or a combination thereof of the first adenovirus nucleic acid sequence, and wherein the second adenovirus nucleic acid fails to encode a 52/55 kDa protein specific for the second adenovirus serotype-specific cis-acting packaging sequence; and
  (iii) a nucleic acid sequence encoding an adenovirus 52/55 kDa protein specific for the first adenovirus serotype-specific cis-acting packaging sequence; and
(b) culturing the host cells under conditions where the first adenovirus sequence is encapsidated to produce a replication defective adenovirus vector.

20. A method of producing an encapsulated a replication defective adenovirus vector, comprising:
(a) transforming or infecting adenovirus replication competent host cells with a first and second adenovirus nucleic acid sequences, wherein the cells comprise a nucleic acid sequence encoding an adenovirus 52/55 kDa trans-acting protein that supports packaging of the first adenovirus nucleic acid sequence and fails to support packaging of the second adenovirus nucleic acid sequence, and wherein
  (i) the first adenovirus nucleic acid sequence comprises:
    5' and 3' adenovirus inverted terminal repeats (ITRs);
    a first adenovirus serotype-specific cis-acting packaging sequence; and
    a heterologous gene operably linked to a transcriptional control sequence,
    wherein the first adenovirus nucleic acid sequence comprises a defective or modified adenovirus E1 gene, E2A gene, E2B gene, E3 gene, E4 gene, E4 promoter, penton gene, fiber gene, hexon gene, or a combination thereof, and wherein the first adenovirus nucleic acid fails to encode a 52/55 kDa trans-acting protein specific for the first cis-acting packing sequence;
  (ii) the second adenovirus nucleic acid sequence comprises:
    5' and 3' adenovirus ITRs;
    a second adenovirus serotype-specific cis-acting packaging sequence,
    wherein the second adenovirus nucleic acid sequence complements the defective or modified adenovirus E1 gene, E2A gene, E2B gene, E3 gene, E4 gene, E4 promoter, penton gene, fiber gene, hexon gene, or a combination thereof of the first adenovirus nucleic acid sequence, and wherein the second adenovirus nucleic acid fails to encode a 52/55 kDa trans acting protein specific for the second adenovirus serotype-specific cis-acting packaging sequence; and
(b) culturing the cells under conditions where the first adenovirus sequence is encapsidated to produce a replication defective adenovirus vector.

21. A method of producing an encapsidated a replication defective adenovirus vector, comprising the following steps:

(a) transforming or infecting adenovirus replication competent host cells with a first and second adenovirus replication defective sequence, wherein
  (i) the first adenovirus nucleic acid sequence comprises:
    5' and 3' adenovirus inverted terminal repeats (ITRs);
    a first adenovirus serotype-specific cis-acting packaging sequence;
    a heterologous gene operably linked to a transcriptional control sequence; and
    a nucleic acid sequence encoding an adenovirus 52/55 kDa protein specific for the first adenovirus serotype-specific cis-acting packaging sequence,
    wherein the first adenovirus nucleic acid sequence comprises a defective or modified adenovirus E1 gene, E2A gene, E2B gene, E3 gene, E4 gene, E4 promoter, penton gene, fiber gene, hexon gene, or a combination thereof; and
  (ii) the second adenovirus nucleic acid sequence comprises:
    5' and 3' adenovirus ITRs;
    a second adenovirus serotype-specific cis-acting packaging sequence,
    wherein the second adenovirus nucleic acid sequence complemerits the defective or modified adenovirus E1 gene, E2A gene, E2B gene, E3 gene, E4 gene, E4 promoter, penton gene, fiber gene, hexon gene, or a combination thereof of the first adenovirus nucleic acid sequence, and wherein the second adenovirus nucleic acid fails to encode a 52/55 kDa trans acting protein specific for the second adenovirus serotype-specific cis-acting packaging sequence; and
(b) culturing the cells under conditions where the first adenovirus sequence is encapsidated to produce a replication defective adenovirus vector.

22. A vector for selectively packaging replication defective nucleic acid sequences in adenovirus capsids, the vector comprising:
  (a) a replication defective adenovirus sequence comprising an adenovirus serotype 7 (Ad7) cis-acting packaging sequence;
  (b) a nucleic acid sequence encoding an adenovirus serotype 5 (Ad5) 52/55 kDa protein; and
  (c) an adenoviral nucleic acid sequence that encodes a viral capsid and fails to encode or produce an adenovirus 7 serotype 52/55 kDa trans-acting protein.

23. A cell for selectively packaging a replication defective adenovirus nucleic acid sequence in an adenovirus capsid, the cell comprising:
  (a) a first adenovirus nucleic acid sequence comprising:
    (i) 5' and 3' adenovirus inverted terminal repeats (ITRs);
    (ii) a first adenovirus serotype-specific cis-acting packaging sequence; and
    (iii) a heterologous nucleic acid operably linked to a transcriptional control sequence,
    wherein the first adenovirus nucleic acid sequence comprises a defective or modified adenovirus E1 gene, E2A gene, E2B gene, E3 gene, E4 gene, E4 promoter, penton gene, fiber gene, hexon gene, or a combination thereof, and wherein the first adenovirus nucleic acid fails to encode a 52/55 kDa trans-acting protein specific for the first cis-acting packing sequence;
  (b) a second adenovirus nucleic acid sequence comprising:
    (i) 5' and 3' adenovirus ITRs;
    (ii) a second adenovirus serotype-specific cis-acting packaging sequence,
    wherein the second adenovirus nucleic acid sequence complements the defective or modified adenovirus E1 gene, E2A gene, E2B gene, E3 gene, E4 gene, E4 promoter, penton gene, fiber gene, hexon gene, or a combination thereof of the first adenovirus nucleic acid sequence, and wherein the second adenovirus nucleic acid fails to encode a 52/55 kDa trans acting protein specific for the second adenovirus serotype-specific cis-acting packaging sequence; and
  (c) a nucleic acid sequence encoding an adenovirus 52/55 kDa trans-acting protein specific for the first adenovirus serotype-specific cis-acting packaging sequence,
    wherein the replication defective adenovirus comprises the first adenovirus nucleic acid sequence.

24. A cell line for selectively packaging a replication defective adenovirus nucleic acid sequence in an adenovirus capsid, the cell line comprising:
  (a) a first adenovirus nucleic acid sequence comprising:
    (i) 5' and 3' adenovirus inverted terminal repeats (ITRs);
    (ii) a first adenovirus serotype-specific cis-acting packaging sequence; and
    (iii) a heterologous nucleic acid operably linked to a transcriptional control sequence,
    wherein the first adenovirus nucleic acid sequence comprises a defective or modified adenovirus E1 gene, E2A gene, E2B genc, E3 gene, E4 gene, E4 promoter, penton gene, fiber gene, hexon gene, or a combination thereof, and wherein the first adenovirus nucleic acid fails to encode a 52/55 kDa trans-acting protein specific for the first cis-acting packing sequence;
  (b) a second adenovirus nucleic acid sequence comprising:
    (i) 5' and 3' adenovirus ITRs;
    (ii) a second adenovirus serotype-specific cis-acting packaging sequence;
    (iii) a nucleic acid sequence encoding an adenovirus 52/55 kDa trans-acting protein that supports packaging of the first adenovirus nucleic acid sequence and fails to support packaging of the second adenovirus nucleic acid sequence,
    wherein the second adenovirus nucleic acid sequence complements the defective or modified adenovirus E1 gene, E2A gene, E2B gene, E3 gene, E4 gene, E4 promoter, penton gene, fiber gene, or a combination thereof of the first adenovirus nucleic acid sequence,
  wherein the replication defective adenovirus comprises the first adenovirus nucleic acid sequence.

25. A kit useful for producing encapsidated adenovirus replication defective nucleic acid sequences, the kit comprising:
  (a) a first adenovirus nucleic acid sequence comprising:
    (i) 5' and 3' adenovirus ITRs;
    (ii) a first adenovirus serotype-specific cis-acting packaging sequence; and
    (iii) a heterologous nucleic acid operably linked to a transcriptional control sequence;
    wherein the first adenovirus nucleic acid sequence comprises a defective or modified adenovirus E1 gene, E2A gene, E2B gene, E3 gene, E4 gene, E4 promoter, penton gene, fiber gene, hexon gene, or a combination thereof, and wherein the first adenovirus nucleic acid fails to encode a 52/55 kDa trans-acting protein specific for the first cis-acting packing sequence;
  (b) a second adenovirus nucleic acid sequence comprising:

(i) 5' and 3' adenovirus ITRs;
(ii) a second adenovirus serotype-specific cis-acting packaging sequence;
(iii) a nucleic acid sequence encoding an adenovirus 52/55 kDa trans-acting protein that supports packaging of the first adenovirus nucleic acid sequence and fails to support packaging of the second adenovirus nucleic acid sequence;
wherein the second adenovirus nucleic acid sequence complements the defective or modified adenovirus E1 gene, E2A gene, E2B gene, E3 gene, E4 gene, E4 promoter, penton gene, fiber gene, hexon gene, or a combination thereof of the first adenovirus nucleic acid sequence; and (c) an adenovirus replication competent host cell;
wherein the replication defective adenovirus comprises the first adenovirus nucleic acid sequence.

* * * * *